United States Patent [19]
Cullinan et al.

[11] Patent Number: 5,908,859
[45] Date of Patent: Jun. 1, 1999

[54] BENZOTHIOPHENES FOR INHIBITING HYPERLIPIDEMIA

[75] Inventors: George Joseph Cullinan, Trafalgar; Patrick Irving Eacho, Indianapolis; Patricia Sue Foxworthy-Mason, Indianapolis; Robert John Schmidt, Indianapolis, all of Ind.

[73] Assignee: Eli Lilly and Company, Indianapolis, Ind.

[21] Appl. No.: 09/128,872

[22] Filed: Aug. 4, 1998

Related U.S. Application Data

[60] Provisional application No. 60/055,483, Aug. 11, 1997.

[51] Int. Cl.$^6$ .................. A61K 31/38; C07D 333/56; C07D 333/60
[52] U.S. Cl. .............................. 514/443; 549/57
[58] Field of Search ................. 549/57; 514/443

[56] References Cited

U.S. PATENT DOCUMENTS

| | | | |
|---|---|---|---|
| 3,274,213 | 9/1966 | Lednicer | 260/326.5 |
| 3,331,854 | 7/1967 | Huffman et al. | 260/330.5 |
| 3,394,125 | 7/1968 | Crenshaw | 260/326.5 |
| 3,413,305 | 11/1968 | Crenshaw | 260/326.5 |
| 3,558,616 | 1/1971 | Brandstrom et al. | 260/247.1 |
| 3,935,231 | 1/1976 | Avar et al. | 260/330.5 |
| 3,947,470 | 3/1976 | Brenner et al. | 260/330.5 |
| 4,075,227 | 2/1978 | Jones et al. | 260/330.5 |
| 4,133,814 | 1/1979 | Jones et al. | 260/326.55 A |
| 4,358,593 | 11/1982 | Jones et al. | 546/202 |
| 4,380,635 | 4/1983 | Peters | 546/202 |
| 4,418,068 | 11/1983 | Jones | 424/267 |
| 4,663,347 | 5/1987 | Atkinson et al. | 514/467 |
| 5,395,842 | 3/1995 | Labrie et al. | 514/320 |
| 5,446,061 | 8/1995 | Bryant et al. | 514/456 |
| 5,470,854 | 11/1995 | von Angerer et al. | 514/233.5 |
| 5,472,962 | 12/1995 | Koizumi et al. | 514/233.5 |
| 5,510,357 | 4/1996 | Palkowitz | 514/324 |

FOREIGN PATENT DOCUMENTS

| | | |
|---|---|---|
| 062 503 A1 | 10/1982 | European Pat. Off. . |
| WO 89/02893 | 4/1989 | WIPO . |
| WO 95/10513 | 4/1995 | WIPO . |
| WO 96/21656 | 7/1996 | WIPO . |

OTHER PUBLICATIONS

Claeys et al., CA 78:58169, 1973.
Croisy et al., CA 101:110665, 1984.
Benassi et al., CA 109:128118, 1988.
Crenshaw, R.R., et al., Potential Antifertility Agents, *J. Med. Chem.* vol. 14, No. 12, pp. 1185–1190 (1971).
Jones, C.D., et al., Antiestrogens, *J. Med. Chem.* vol. 27, pp. 1057–1066 (1984).
Jones, C.D., et al., Antiestrogens, *J. Med. Chem.* vol. 35, pp. 931–938 (1992).

*Primary Examiner*—Laura L. Stockton
*Attorney, Agent, or Firm*—Scott Alexander McNeil; James J. Sales

[57] ABSTRACT

The present application relates to a series of compounds, and pharmaceutical formulations thereof, of the formula

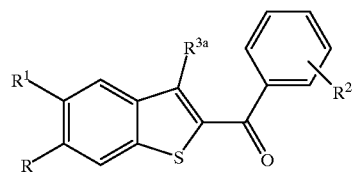

which provide a method of inhibiting hyperlipidemia, especially hypercholesterolemia, and the pathological sequelae thereof, in mammals, including humans.

24 Claims, No Drawings

BENZOTHIOPHENES FOR INHIBITING HYPERLIPIDEMIA

COMPOUNDS AND USES THEREOF

This application claims the benefit of U.S. Provisional application No. 60/055,483, filed Aug. 11, 1997.

FIELD OF THE INVENTION

The current invention relates to the fields of medicinal organic chemistry, pharmacology, and medicine. Further, the current invention relates to a group of known and novel compounds which demonstrate the potential for treating a pathological state known as hyperlipidemia in mammals, including humans.

BACKGROUND OF THE INVENTION

Hyperlipidemia is a pathological state in mammals, where there is an abnormally high concentration of lipids circulating in the serum. The composition of the lipid pool in the circulation consists mostly of triglyceride (fatty acid esters of glycerol), cholesterol, and fatty acid esters of cholesterol. Such lipophillic molecules are poorly soluble in the aqueous environment of the serum and are, therefore, rarely found as free entities in the circulation. Such molecules are generally found bound to specific proteins in the form of complexes which act as transporting mechanisms. The specific, lipid carrying proteins are known as a class as apoproteins. Various combinations of different and specific lipids and apoproteins form particles (lipoproteins) which serve both to transport lipids and perform specific biological functions. In general, such particles are physically classified by their density, e.g., high density lipoproteins (HDL)—1.063–1.210 g/mL, low density lipoproteins (LDL)—1.019–1.063 g/mL, very low lipoproteins (VLDL)—<1.006 g/mL, etc. In addition, each of these particles contains a specific profile of lipid composition, e.g., HDL contains mostly cholesterol and its esters, whereas LDL's contain more or exclusively triglycerides.

Common pathological sequelae of hyperlipidemia, especially hypercholesterolemia, are atherosclerosis, hypertension, ischemic events, such as, myocardial infarction, cerebral stroke, and organ insufficiency and thrombosis.

A commonly used index of identifying human patients at risk of the pathological sequelae of hyperlipidemia, is the determination of total serum cholesterol. Generally, in adults, total serum cholesterol levels greater than 240 mg/dL are indicative of potential danger of hyperlipidemia, while levels<200 mg/dL are considered normal. As a rough measurement, these criteria are reasonably accurate. However, total cholesterol does not reflect the relative amounts or ratio of cholesterol in the various lipoproteins, e.g., HDL versus LDL. This ratio of the distribution of cholesterol has also been shown to correlate to the potential risk of developing cardiovascular disease due to hyperlipidemia. Thus, the total amount of cholesterol and its distribution are risk factors.

In a large and long epidemiologic study (Framingham Study), it was shown that hyperlipidemia, especially hypercholesterolemia, is a risk factor for atherosclerosis. However, this study also demonstrated that a high ratio of HDL to LDL decreases the chances of developing atherosclerosis. Therefore, in order to treat or prevent hyperlipidemia, this study suggests that it is more efficacious to both lower the total serum cholesterol and to raise the ratio of HDL to LDL than to only lower total cholesterol levels.

Many drugs are available which lower total serum cholesterol, e.g., the chemical classes known as the statins. These agents have been useful in both treating and preventing hyperlipidemia. However, these agents have little or no effect on the ratio of HDL to LDL.

Agents or life-styles are known to effect the HDL-LDL ratio, e.g., exercise raises HDL, smoking lowers HDL, small amounts of alcohol raise HDL, and hormones may either raise or lower the ratio. Most germane, to the current invention, is the effect which estrogen has on the HDL–LDL ratio.

Premenopausal women, normally, have higher levels of HDL than their male counterparts. Premenopausal women also have less cardiovascular disease, especially disease related to hyperlipidemia, as compared to males in the same age group. However, postmenopausal women, or women at the menopause, have an increased risk for cardiovascular disease sometimes even surpassing the risk of their male counterparts. At the menopause, women demonstrate a rapid rise in total serum cholesterol and a lowering of HDL. The exact mechanism of this change is not well understood; however, women, who receive Hormone Replacement Therapy, HRT, (estrogens and/or progestins), show a normalization of total serum cholesterol, HDL14 LDL ratio, and a lessening in the risk of cardiovascular disease. Estrogen is believed to exert one of its cardiovascular protecting effects by increasing HDL levels.

Although there are many factors controlling the levels of HDL which are known, the entire control mechanism is not totally understood. One factor thought to be important in this process is the effect of hepatic lipase. Hepatic lipase, a liver enzyme, is a major factor in controlling the degradation of HDL particles. This enzyme facilitates the hydrolysis of HDL phospholipids and triglycerides and the subsequent dissolution of the lipoprotein particle. Recently, it has been found that the gene coding for this enzyme, controlled by many factors, is down-regulated by the hormone estrogen. This down-regulation of the lipase gene and subsequent lowering of the production of the enzyme, may, at least in part, explain the rise in HDL and lowering of cardiovascular risk in postmenopausal women on HRT. (For further information see: "Harrison's Principles of Internal Medicine", Eds. Iselbacher, et al., 9th Ed., McGraw-Hill Co., NYC, Chap. 250, pp. 1159–1168 and Chap.99, pp.507–518 and references therein; and Oka, K. et al., "Transcription of the human lipase gene is modulated by multiple negative elements in HepG2 cells.", Gene, 180, p.69–80 (1996) and references therein.)

Today, HRT is used in women to ameliorate the cardiovascular effects of menopause. This therapy, while effective, suffers from poor patient compliance, due to unpleasant side-effects, poor oral absorption, and poor bio-availability of the natural estrogens 17b-estradiol and estrone.

Compounds of the current invention, i.e., the compounds of formula I(b), have the potential of down regulating the expression of hepatic lipase, thus raising the levels of HDL. This effect of raising HDL indicates usefulness in treating hyperlipidemia, especially hypercholesterolemia, and its subsequent pathological sequelae. In addition, compounds of the current invention are well absorbed by the oral route and possess favorable bio-availability properties.

SUMMARY OF THE INVENTION

The current invention relates to compounds of formula I(a):

I(a)

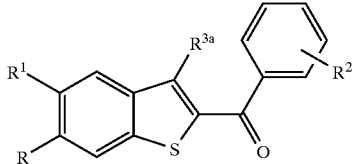

wherein:

R, $R^1$, and $R^2$ are independently at each occurrence hydrogen, hydroxy, or —O—Pg;

Pg is a hydroxy protecting group;

$R^3a$ is hydrogen, $C_1$–$C_6$ alkyl, $C_3$–$C_6$ cycloalkyl, or a moiety of the formula (a), (b), or (c):

(a)

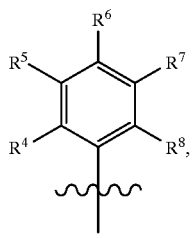

(b)

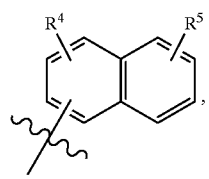

(c)

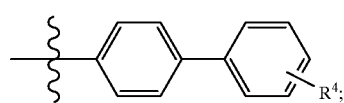

wherein $R^4$, $R^5$, $R^6$, $R^7$, and $R^8$ are independently at each occurrence hydrogen, fluoro, chloro, bromo, $C_1$–$C_4$ alkyl, $C_3$–$C_6$ cycloalkyl, or $C_1$–$C_4$ alkoxy, with the proviso that, in a moiety of formula (a), $R^4$, $R^5$, $R^{6,}$ $R^7$, and $R^8$ can not all be hydrogen;

or a pharmaceutically acceptable salt or solvate thereof, which are useful for inhibiting hyperlipidemia or useful as intermediates to compounds that are useful for inhibiting hyperlipidemia.

Further, the current invention provides methods of inhibiting hyperlipidemia, especially hypercholesterolemia, and the pathological sequelae thereof, in mammals, including humans, which includes administering to a mammal in need thereof an effective amount of a compound of formula I(b):

I(b)

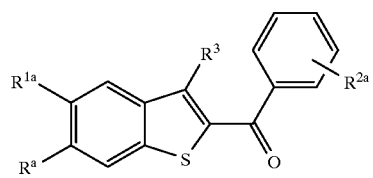

wherein:

$R^a$, $R^{1a}$, and $R^{2a}$ are independently at each occurrence hydrogen, hydroxy, —O($C_1$–$C_4$ alkyl), —OCO($C_1$–$C_4$ alkyl), —OCOAr, —OCO$_2$ ($C_1$–$C_4$ alkyl), —OCO$_2$Ar, or $C_3$–$C_6$ cycloalkoxy;

Ar is phenyl or substituted phenyl;

$R^3$ is hydrogen, $C_1$–$C_6$ alkyl, $C_3$–$C_6$ cycloalkyl, or a moiety of the formula (a), (b), or (c):

(a)

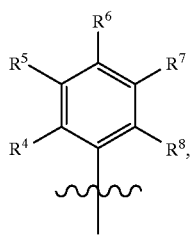

(b)

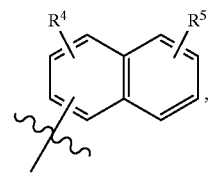

(c)

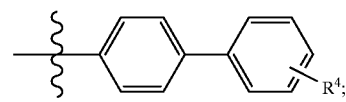

wherein $R^4$, $R^5$, $R^6$, $R^7$, and $R^8$ are independently at each occurrence hydrogen, fluoro, chloro, bromo, $C_1$–$C_4$ alkyl, $C_3$–$C_6$ cycloalkyl, or $C_1$–$C_4$ alkoxy; or a pharmaceutically acceptable salt or solvate thereof.

Further the current invention includes pharmaceutical formulations, comprising a compound of formula I(a), where —O—Pg is —O($C_1$–$C_4$ alkyl), —OCO($C_1$–$C_4$ alkyl), —OCOAr, —OCO$_2$ ($C_1$–$C_4$ alkyl), —OCO$_2$Ar, or $C_3$–$C_6$ cycloalkoxy, and pharmaceutically acceptable excipients.

DETAILED DESCRIPTION OF THE INVENTION

General chemical terms used in the description of compounds herein described bear their usual meanings. For example, "$C_1$–$C_4$ alkyl" refers to a methyl, ethyl, propyl, iso-propyl, n-butyl, s-butyl, or a t-butyl group. The term, "$C_1$–$C_6$ alkyl" would include the $C_1$–$C_4$ alkyl in addition to straight or branched aliphatic chains of 5 or 6 carbon atoms, e.g., pentyl, 2-methylbutyl, hexyl, 2-methylpentyl, 3-methylpentyl, and the like. The term "$C_1$–$C_4$ alkoxy" refers to a methoxy, ethoxy, propoxy, iso-propoxy, t-butoxy, s-butoxy, or a n-butoxy group. The term, "$C_3$–$C_6$ cycloalkyl" means a cyclopropyl, cyclobutyl, cyclopentyl, or a cyclohexyl group. The term "$C_3$–$C_6$ cycloalkoxy" refers to a cylclopropoxy, cyclobutoxy, cyclopentoxy or a cyclohexoxy group.

The symbol "Ar" refers to a phenyl or substituted phenyl group.

The term "substituted phenyl" refers to a phenyl group having one to three substituents selected from the group consisting of $C_1$–$C_4$ alkyl, $C_1$–$C_4$ alkoxy, hydroxy, nitro, chloro, fluoro, or tri(chloro or fluoro)methyl.

The terms "halide" or "halo" refer to chloro, bromo, or iodo.

The term "suitable kinetic base" refers to a base which provides a non-reversible deprotonation of an acidic substrate and is reactive enough to effect the desired reaction without significantly effecting any undesired reactions. Examples of kinetic bases include, but are not limited to, alkyl metals (e.g. n-butyl lithium, s-butyl lithium, and t-butyl lithium or ethyl magnesium bromide), metal amides such as lithium diisopropyl amide, metal alkoxides such as potassium t-butoxide, or metal hydrides (e.g. sodium, lithium, or potassium hydride).

The term "carbonyl activating group" refers to a substituent of a carbonyl that promotes nucleophilic addition reactions at that carbonyl. Suitable activating substituents are those which have a net electron withdrawing effect on the carbonyl. Such groups include, but are not limited to, esters and amides such as hydroxybenzotriazole, imidazole, a nitrophenol, pentachlorophenol, N-hydroxysuccinimide, dicyclohexylcarbodiimide, N-hydroxy-N-methoxyamine, and the like; acid anhydrides such as acetic, formic, sulfonic, methanesulfonic, ethanesulfonic, benzenesulfonic, or p-tolylsulfonic acid anhydride, and the like; and acid halides such as the acid chloride, bromide, or iodide.

The term "hydroxy protecting group" denotes a group understood by one skilled in the organic chemical arts of the type described in Chapter 2 of "Protective Groups in Organic Synthesis", 2nd Edition, T. H. Greene, et al., John Wiley & Sons, New York, 1991, hereafter "Greene".

Representative hydroxy protecting groups include, for example, $C_1$–$C_4$ alkyl ether groups, including methyl, ethyl, or isopropyl ether; substituted $C_1$–$C_4$ alkyl ether groups, including methoxymethyl ether, methylthiomethyl ether, tert-buylthiomethyl ether, (phenyldimethylsilyl)methoxymethyl ether, benzyloxymethyl ether, ρ-methoxybenzyloxymethyl ether, and tert-butoxy-methyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; and $C_3$–$C_6$ cycloalkyl ether groups, including cyclopentyl ether and cyclohexyl ether; phenyl and substituted phenyl ether groups such as phenyl ether, ρ-chlorophenyl ether, ρ-methoxyphenyl ether, and 2,4-dinitrophenyl ether; benzyl ether groups such as benzyl ether; and alkylsilyl ether groups such as trimethyl- triethyl- and triisopropylsilyl ethers, mixed alkylsilyl ether groups such as dimethylisopropylsilyl ether, and diethylisopropylsilyl ether; and ester groups of the general formula $CO_2C_1$–$C_6$ alkyl or $CO_2Ar$, or specific esters such as formate ester, benzylformate ester, mono- di- and trichloroacetate esters, phenoxyacetate ester, and ρ-chlorophenoxyacetate, and the like. Acyl groups of the general formula $CO(C_1$–$C_6$ alkyl) or COAr and sulfonyl groups of the general formula $SO_2R^9$, where $R^9$ is Ar or $C_1$–$C_4$ alkyl, are also encompassed within the definition of hydroxy protecting group.

In general, the species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). However, the skilled artisan will recognize that the definition of $R^a$, $R^{1a}$, and $R^{2a}$ in compounds of formula I(b) includes hydroxy protecting groups which form a subset of the hydroxy protecting groups listed above. Thus, to carry out the methods of the invention, the species of hydroxy group is important and only those groups embodied within the method claims are operative. For purposes of synthesizing compounds of formula I(a) or I(b), it is within the knowledge of one skilled in the art to select appropriate hydroxy protecting group(s) for a given set of reaction conditions given the guidance provided by Greene cited above.

The term "pharmaceutically acceptable salt" refers to base addition salts of compounds of formula I(a) or I(b) which are known to be non-toxic and are commonly used in the pharmaceutical literature. Commonly used basic addition salts would be the salts formed by: alkali or alkaline earth hydroxides, ammonium hydroxide, sodium hydroxide, alkyl or aromatic amines, and the like.

By "pharmaceutically acceptable" it is also meant that the carrier, diluent, excipients and salt must be compatible with the other ingredients of the formulation, in addition to, not being deleterious to the recipient thereof.

The term "solvate" represents an aggregate that comprises one or more molecules of the solute, such as a formula I(a) or I(b) compound, with one or more molecules of solvent.

As used herein, the term "effective amount" means an amount of a compound of formula I(b) which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

The term "inhibit" bears its usual meaning which includes prohibiting, ameliorating, halting, restraining, preventing, slowing or reversing the progression, or reducing the severity of hyperlipidemia or a pathological symptom related to or resultant from hyperlipidemia, especially hypercholesterolemia. As such, these methods include both medical therapeutic (acute) and/or prophylactic (prevention) administration as appropriate.

Synthesis

Compounds of formula I(a) which encompass all the compounds of formula I(b) except those where R3 is a moiety of formula (a) wherein $R^4$, $R^5$, $R^6$, $R^7$, and $R^8$ are all hydrogen, may be synthesized by the routes illustrated in Scheme 1 and 2 below. Compounds of formula I(b), where $R^3$ is a moiety of formula (a) where $R^4$, $R^5$, $R^6$, $R^7$, and $R^8$ are all hydrogen, can be prepared by analogy to the methods discussed in Schemes 1 and 2 below. In Schemes 1 and/or 2, Halo, R, $R^1$, $R^2$, $R^{3a}$ are as described supra.

SCHEME 1

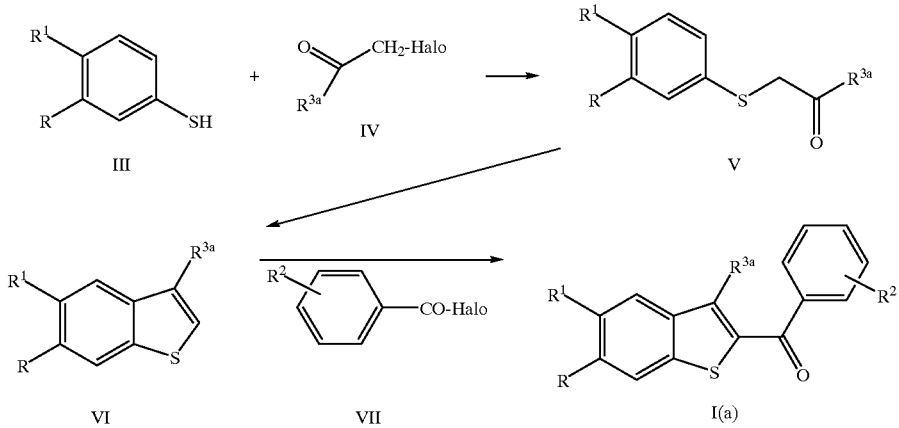

Briefly, the synthesis begins with S-alkylation of a thiophenol of formula III with a compound of formula IV to form the sulfides of formula V. These types of S-alkylations are well known in the literature and may be accomplished by a variety of methods and reaction conditions. For example, the two reactants may be heated in the presence of a strong, tertiary, organic base, e.g. pyridines, trialkylamines, lutidines and the like. Additionally, the same synthesis may be accomplished reacting the thiophenol with a strong inorganic base, such as sodium carbonate, potassium hydroxide, and the like to generate a sulfide anion which may subsequently be reacted with the compound of formula IV. Two particularly preferred compounds of formula III are 3-methoxythiophenol and 4-methoxythiophenol. A preferred formula IV compound is one where "halo" is bromo.

The sulfides of formula V are dehydrated and ring closed to form the benzo[b]thiophenes of formula VI. This reaction may be accomplished by heating a compound of formula V in the presence of a strong mineral or organic acid e.g., aryl or alkylsulfonic acids, sulfuric acid, polyphosphoric acid, and the like.

The next step in this synthetic sequence involves the acylation in the 2-position of the benzo[b]thiophene (VI) with a compound of formula VII to yield the 2-aroyl-benzo[b]thiophenes of formula I(a). This acylation may be performed under standard Friedel-Crafts conditions, i.e., in the presence of a Lewis acid in inert solvents (for further information see: Olah, G., "Friedel-Crafts and Related Reactions", Interscience Publications, New York, London, and Sidney, 1963, Vol. I, Ch. III and IV). Preferred acid catalyst would be $AlCl_3$ in a halogenated hydrocarbon, such as dichloroethane. A preferred compound of formula VII is 4-methoxybenzoyl chloride.

Alternately, compounds of formula I(a) may be prepared by the synthetic pathway illustrated in Scheme 2 below where Y is a carbonyl activating group.

SCHEME 2

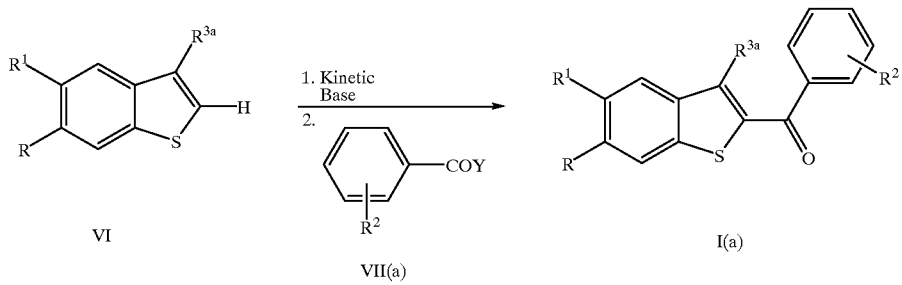

Compounds of formula I(a) may be prepared by reacting a compound of formula VI with a kinetic base to generate an anion at the 2 position of the benzo[b]thiophene ring system and then adding a compound of formula VII(a). Suitable kinetic bases would include, but not be limited to, n-butyl lithium, sodium hydride, and the like. This reaction is generally run in inert solvents, such as hexanes, tetrahydrofuran, halohydrocarbons, and the like. The addition of the base, formation of the anion, and the addition of the compound of formula VII(a) is generally performed at low temperatures (e.g. 0° C. to −78° C.) and under an inert atmosphere such as a nitrogen atmosphere. Once all the reactants are combined, the reaction may be allowed to continue at a low temperature or may be allowed to warm slowly to room temperature.

When any of R, $R^a$, $R^1$, $R^{1a}$, $R^2$, or $R^{2a}$ are hydroxy protecting groups in compounds of formula I(a) or I(b), they may be removed by well known methods in the art. Numerous reactions for the formation and removal of the hydroxy protecting groups contemplated within the scope of this invention are described in a number of standard works including, for example in *The Peptides,* Vol. I, Schrooder and Lubke, Academic Press (London and New York, 1965) or in Greene. Methods for removing preferred hydroxy protecting groups, particularly methyl groups, are essentially as described in Example 2 infra. In addition, if compounds of formula I(a) contain a hydroxy protecting group(s) which is not operative in the methods of the current invention, it may be removed and an operative hydroxy protecting group(s) may be installed as described in Greene or as described in the paragraph below.

Compounds of formula I(a) or I(b), where R, $R^a$, $R^1$, $R^{1a}$, $R^2$, or $R^{2a}$ are acyl derivatives of the free phenols, may be obtained by removal of the non-acyl hydroxy protecting groups when present and acylation with the appropriate acylating agent. Compounds of formula I(a), where R, $R^1$, and $R^2$ are sulfonyl derivatives of the free phenols, may be obtained by removal of the non-sulfonyl hydroxy protecting groups when present and sulfonation with the appropriate sulfonating agent. Methods for the acylation or sulfonation of the deprotected compounds is essentially revealed in U.S. Pat. No. 4,358,593, the teachings of which are herein incorporated by reference.

For specific instruction on the synthesis of compounds of formula I(b) where $R^3$ is phenyl see U.S. Pat. No. 4,075,227 the teaching of which are hereby incorporated by reference.

The optimal time for performing the reactions of Schemes 1 and 2 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. Intermediate and final products may be purified, if desired by common techniques such as recrystallization or chromatography over solid supports such as silica gel or alumina.

Compounds of formula III, IV, VII and VII(a) are either commercially available or may be prepared by methods well known in the art.

Application of the above chemistry enables the synthesis of the compounds of formula I(a), which include, but is not limited to:

2-benzoylbenzo[b]thiophene;
2-(4-methoxybenzoyl)-3-methylbenzo[b]thiophene;
2-(3-methoxybenzoyl)-3-cyclopentylbenzo[b]thiophene;
2-(4-methoxybenzoyl)-3-(4-fluorophenyl)-5-hydroxybenzo[b]thiophene;
2-(4-methoxybenzoyl)-3-napthyl-6-hydroxybenzo[b]thiophene;
2-(4-hydroxybenzoyl)-3-(4-phenylphenyl)-5-hydroxybenzo[b]thiophene;
2-(4-hydroxybenzoyl)-3-(4-bromophenyl-6-hydroxybenzo[b]thiophene;
2-(4-methoxybenzoyl)-3-(2,3-difluorophenyl-5-methoxybenzo[b]thiophene;
2-(4-methoxybenzoyl)-3-cyclobutyl-6-methoxybenzo[b]thiophene;
2-(3-methoxybenzoyl)-3-cyclopropyl-5-hydroxybenzo[b]thiophene;
2-(3-methoxybenzoyl)-3-cyclohexyl-6-hydroxybenzo[b]thiophene;
2-(4-acetyloxybenzoyl)-3-(2,4,6-trifluorophenyl)-6-methoxybenzo[b]thiophene;
2-(4-benzoyloxybenzoyl)-3-(3-fluoronapthyl-6-methoxybenzo[b]thiophene;
2-(4-methoxybenzoyl)-3-(3-fluoro-4-phenylphenyl)-6-acetyloxybenzo[b]thiophene;
2-(4-cyclopentyloxybenzoyl)-3-(3,7-difluronapthyl-6-hydroxybenzo[b]thiophene;
2-(3-cyclopentyloxybenzoyl)-3-(3-fluoro-4-methoxyphenyl)-6-hydroxybenzo[b]thiophene;
2-(4-cyclopentyloxybenzoyl)-3-(3,4,5-trifluorophenyl)-5-hydroxybenzo[b]thiophene;
2-(4-hydroxybenzoyl)-3-cyclobutyl-6-hydroxybenzo[b]thiophene;
2-(4-methoxybenzoyl)-3-methyl-5-hydroxybenzo[b]thiophene;
2-(4-methoxybenzoyl)-3-ethyl-6-hydroxybenzo[b]thiophene;
2-(4-methoxybenzoyl)-3-isopropyl-6-hydroxybenzo[b]thiophene;
2-(4-hydroxybenzoyl)-3-butyl-6-hydroxybenzo[b]thiophene;
2-(4-hydroxybenzoyl)-3-(4-methylphenyl)-6-hydroxybenzo[b]thiophene;
2-(4-hydroxybenzoyl)-3-(3-methylphenyl)-6-hydroxybenzo[b]thiophene;
2-(4-methoxybenzoyl)-3-(2-methyphenyl)-6-hydroxybenzo[b]thiophene;
2-(4-hydroxybenzoyl)-3-(3,5-dimethylphenyl)-6-hydroxybenzo[b]thiophene;
2-(4-hydroxybenzoyl)-3-(4-chlorophenyl)-6-hydroxybenzo[b]thiophene;
2-(4-acetyloxybenzoyl)-3-(4-methylphenyl)-6-hydroxybenzo[b]thiophene;
2-(4-hydroxybenzoyl)-3-(4-methylphenyl)-6-benzoyloxybenzo[b]thiophene; and the like.

The following Preparations and Examples are provided for the purpose of illustrating the preparation of the compounds of the current invention and are not intended to limit its scope.

In the following Preparations and Examples, the terms melting point, proton nuclear magnetic resonance spectra, field desorption mass spectra, elemental analysis, high performance liquid chromatography, and thin layer chromatography are abbreviated "mp", "$^1$H NMR", "MS(FD)", "EA", "HPLC", and "TLC", respectively. The values reported for MS(FD) correspond to mass numbers unless otherwise indicated.

PREPARATIONS

Preparation 1

3-Phenylbenzo[b]thiophene

Step 1: Preparation of a-(Phenylthio)acetophenone

To 300 mL of pyridine was added a-bromoacetophenone (150 g, 750 mmol) and thiophenol (83 g, 750 mmol). The mixture was heated at reflux for six hours. The pyridine was evaporated and the residue dissolved in ethyl acetate. The ethyl acetate solution was washed exhaustively with 1 N sodium hydroxide, then with 1 N hydrochloric acid, dried over magnesium sulfate, filtered, and evaporated to yield a brown oil. The product was crystallized from ethanol at 0° C. to yield 116 g of the title compound.

mp 52° C.–53° C. EA calculated for $C_{14}H_{12}OS$: C, 73.65; H, 5.30; O, 7.01; S,14.04. Found: C, 73.46; H, 5.50; O, 7.25; S, 14.30.

Step 2: Preparation of 3-Phenylbenzo[b]thiophene a-(Phenylthio)acetophenone (116 g) was cyclized by heating it in polyphosphoric acid on a steam bath at 90° C. for two hours. From the product mixture was obtained crude product which was chromatographed on a silica gel column eluting with a mixture of petroleum ether-benzene to obtain the title compound.

Preparation 2

6-Methoxy-3-Phenylbenzo[b]thiophene

3-Methoxythiophenol was converted to the title compound by the procedure of Preparation 1 to give a white solid.

mp: 58° C.–59° C.

Preparation 3 p-Cyclopentyloxybenzoyl Chloride

To 50 g of methyl p-hydroxybenzoate were added 82 g of cyclopentyl bromide. The mixture was cooled to 0° C. and 24 g of sodium hydride (in a 50% mineral oil suspension) were added in small portions. Ice bath cooling was continued until the resulting effervescence terminated. The reaction mixture then was heated to 75° C. for four hours, cooled, and 25 mL of ethanol was added dropwise. The resulting mixture was evaporated to dryness, and the residue was dissolved in a mixture of water and ether. The ether layer was separated and washed with cold 5% aqueous sodium hydroxide and then with water. The ether layer then was dried over magnesium sulfate and evaporated to dryness to give about 72 g of crude methyl p-cyclopentyloxybenzoate. The crude ester was added to 400 mL of ethylene glycol containing 100 g of potassium hydroxide. The mixture was refluxed for several hours and then was transferred to a 4 L beaker. A mixture of ice and water was added. The resulting mixture then was placed in a separatory funnel and was washed with ether. The aqueous layer was acidified by addition of concentrated hydrochloric acid. The resulting precipitate was collected by filtration, washed with water, and recrystallized from methanol to obtain 44.1 g of p-cyclopentyloxybenzoic acid. A solution of 8.7 g (0.024 mole) of p-cyclopentyloxybenzoic acid in 250 mL of anhydrous ether was prepared. The solution was cooled to 5° C.–10° C. and 8.85 g of thionyl chloride followed by two drops of pyridine were added. The mixture was allowed to warm to room temperature and was stirred overnight. The mixture then was evaporated to dryness, and the oily residue of p-cyclopentyloxybenzoyl chloride was dissolved in 150 mL of 1,2-dichloroethane for use as described in Example 10 below.

EXAMPLES

Example 1
2-(4-Methoxybenzoyl)-3-Phenylbenzo[b]thiophene

To a stirred slurry of aluminum chloride (14.6 g, 110 mmol) in 1,2-dichloroethane at 0° C. was added 4-methoxybenzoylchloride (18.7 g, 110 mmol). The mixture was stirred at 0° C. for ten minutes, and 3-phenylbenzo[b]thiophene (21.0 g, 100 mmol) in 1,2-dichlororethane was added. The mixture was stirred for two hours, with the temperature maintained at 0° C. The reaction mixture was poured into a mixture of ice and hydrochloric acid. The resulting mixture was extracted with ether. The ether extract was washed with water, aqueous sodium bicarbonate, and then again with water. The ether layer was dried over magnesium sulfate and evaporated to dryness. The residue was dissolved in ethanol and kept at 5° C. for three days. The product crystallized out, yielding 23.7 g of the title compound. mp: 94° C.–95° C. EA calculated for $C_{22}H_{16}O_2S$: C, 76.72; H, 4.68; O, 9.29. Found: C, 76.54; H, 4.74; O, 9.25.

Example 2
2-(4-Hydroxybenzoyl)-3-Phenylbenzo[b]thiophene

A mixture of 2-(4-methoxybenzoyl)-3-phenylbenzo[b]thiophene (12.0 g) and pyridine hydrochloride (35 g) was refluxed for thirty minutes. The hot reaction mixture was poured onto ice and the mixture transferred to a blender, homogenized, and the resulting crystals were collected by filtration, washed with water, and dried in vacuo at 80° C. yielding 11 g of the title compound.

mp: 204° C.–205° C. EA calculated for $C_{21}H_{14}O_2S$: C, 76.34; H, 4.27; S, 9.70. Found: C, 76.11; H, 4.22; S, 10.00.

Example 3
2-Benzoyl-3-Phenyl-6-Methoxybenzo[b]thiophene

3-Phenyl-6-methoxybenzo[b]thiophene and benzoyl chloride were converted to the title compound by the procedure of Example 1 in 52% yield, after crystallization from methanol.

mp: 94° C.–95.5° C. EA calculated for $C_{22}H_{16}O_2S$: C, 76.72; H, 4.68; O, 9.29; S, 9.31. Found: C, 76.51; H, 4.90; O, 9.08; S, 9.13.

Example 4
2-(4-Methoxybenzoyl)-3-Phenyl-6-Methoxybenzo[b]thiophene

3-Phenyl-6-methoxybenzo[b]thiophene and 4-methoxybenzoyl chloride were converted to the title compound by the procedure of Example 1 in 91% yield, after crystallization from methanol.

mp: 127° C.–128° C. EA calculated for $C_{23}H_{18}O_3S$: C, 73.77; H, 4.85; O, 12.82; S, 8.56. Found: C, 74.17; H, 5.00; O, 12.93; S, 8.36.

Example 5
2-(4-Hydroxybenzoyl)-3-Phenyl-6-Hydroxybenzo[b]thiophene 2-(4-Methoxybenzoyl)-3-phenyl-6-methoxybenzo[b]thiophene was converted to the title compound by the procedure of Example 2 in 65% yield, after crystallization from ethyl acetate-benzene.

mp: 198° C.–200° C.

Example 6
2-(3-Methoxybenzoyl)-3-Phenyl-6-Methoxybenzo[b]thiophene

3-Phenyl-6-methoxybenzo[b]thiophene and 3-methoxybenzoyl chloride were converted to the title compound by the procedure of Example 1 in 82% yield, after crystallization from methanol.

mp: 101° C.–103° C. EA calculated for $C_{23}H_{18}O_3S$: C, 73.27; H, 4.85; O, 12.82; S, 8.56. Found: C, 74.14; H, 4.83; O, 12.38; S, 8.48.

Example 7
2-(3-Hydroxybenzoyl)-3-Phenyl-6-Hydroxybenzo[b]thiophene 2-(3-Methoxybenzoyl)-3-phenyl-6-methoxybenzo[b]thiophene was converted to the title compound by the procedure of Example 2 in 91% yield, after crystallization from methanol.

mp: 202° C.–202.5° C. EA calculated for $C_{21}H_{14}O_3S$: C, 72.81; H, 4.07; O, 13.86; S, 9.26. Found: C, 72.70; H, 3.94; O, 13.57; S, 9.50. MS(FD): 346 (M+).

Example 8
2-(2-Methoxybenzoyl)-3-Phenyl-6-Methoxybenzo[b]thiophene

3-Phenyl-6-methoxybenzo[b]thiophene and 2-methoxybenzoyl chloride were converted to the title compound by the procedure of Example 1 in 97% yield, after crystallization from methanol.

mp: 111° C.–112° C. EA calculated for $C_{23}H_{18}O_3S$: C, 73.77; H, 4.85; O, 12.82. Found: C, 73.96; H, 4.77; O, 12.60.

Example 9
2-(2-Hydroxybenzoyl)-3-Phenyl-6-Hydroxybenzo[b]thiophene 2-(2-Methoxybenzoyl)-3-phenyl-6-methoxybenzo[b]thiophene was converted to the title compound by the procedure of Example 2 and isolated as an oil. The product was crystallized from benzene-hexane (2:1) (v/v).

mp: 123° C.–124° C. EA calculated for $C_{21}H_{14}O_3S$: C, 72.81; H, 4.07; O, 13.86; S, 9.26. Found: C, 72.88; H, 4.19; O, 13.77; S, 8.58. MS(FD): 346 (M+).

Example 10
2-(4-Cyclopentyloxybenzoyl)-3-Phenyl-6-Methoxybenzo[b]thiophene

3-Phenyl-6-methoxybenzo[b]thiophene and p-cyclopentyloxybenzoyl chloride were converted to the title compound by the procedure of Example 1 to yield 6 g of crude product.

Example 11
2-(4-Cyclopentyloxybenzoyl)-3-Phenyl-6-Hydroxybenzo[b]thiophene

To 100 mL of dry N,N-dimethylformamide were added 5.0 g (0.014 mol) of the crude benzothiophene from Example 10 and 1.2 g (0.05 mol) of sodium hydride. The mixture was cooled to 0° C. under nitrogen. Ethyl mercaptan (3.1 g, 0.05 mol) was added to the mixture by means of a syringe. When the resulting effervescence ceased the reaction mixture was heated to 90° C. overnight. To the resulting reaction mixture then were added dropwise 25 mL of ethanol. The resulting mixture was evaporated to dryness, and the residue was dissolved in a mixture of water and ether. The ether layer was separated and washed with dilute hydrochloric acid and dilute sodium hydroxide. The ether layer then was dried over magnesium sulfate and evaporated to give a yellow oil which was chromatographed over silica using a solvent gradient ranging from 100% benzene to a mixture of 90% benzene and 10% ethyl acetate to yield about 3 g of the title compound.

EA calculated for $C_{26}H_{22}O_3S$: C, 75.34; H, 5.35; O, 11.58. Found: C, 75.61; H, 5.58; O, 11.43.

The following examples demonstrating the methods of the current invention are given for the purpose of illustration and are not meant to be limiting in any way.

ASSAY 1

Seventy-five day old female Sprague Dawley rats (weight range of 200 g to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: xylazine (2:1, V:V) mixture and a blood sample was collected by cardiac puncture.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Representative compounds of formula I(b), when assayed by this method, gave the positive results reported in Table 1 below.

TABLE 1

| Compound | Serum Cholesterol (% decrease vs Control) |
|---|---|
| 2-(4-Hydroxybenzoyl)-3-phenyl-6-hydroxybenzo[b]thiophene | 96.5* @ 0.1[a] |
|  | 97.4* @ 1.0[a] |
| (Compound of Example 5) | 95.5* @ 10.0[a] |
| 2-(4-Cyclopentyloxybenzoyl)-3-phenyl-6-hydroxybenzo[b]thiophene | 40.7* @ 0.05[a] |
|  | 54.3* @ 0.1[a] |
|  | 89.4* @ 1.0[a] |
| (Compound of Example 11) | 97.4* @ 10.0[a] |
| 2-(4-Hydroxybenzoyl)-3-phenyl-benzo[b]thiophene | -5 @ 0.1[a] |
|  | 53.6* @ 1.0[a] |
| (Compound of Example 1) | 74.8* @ 10.0[a] |
| 2-(2-Methoxybenzoyl)-3-phenyl-6-methoxybenzo[b]thiophene | 11.3 @ 0.1[a] |
|  | 48.8* @ 1.0[a] |
| (Compound of Example 8) | 71.4* @ 10.0[a] |
| 17a-ethynylestradiol | 78.4* @ 0.1[a] |

*p < 0.05
[a]Dose in mg/kg P.O.

ASSAY 2

Forty-one to forty-three day old Sprague Dawley male rats (weight range 200 g to 225 g) were obtained from Harlan (Indianapolis, Ind.). Upon arrival, the animals were housed in metal hanging cages with 6 or 7 animals per cage, with access to food and water, ad libitum. After one or two days, the animals were housed individually, ambient temperature was maintained at 22.2° C. with a relative humidity of 40%. The photoperiod in the room was 12 hours of dark and 12 hours of light.

Dosing Regimen Tissue Collection. After a one week acclimation period daily dosing with the test compounds or standards was initiated. The animals were weighed after two days of dosing and the doses were adjusted for any change in the animals weight. All compounds were given by oral gavage in a formulation of 0.5 mL of 1% aqueous carboxymethylcellulose. The animals were dosed for four days. At the end of the dosing period, the animals were weighed and rendered unconscious with carbon dioxide. Blood samples were collected by cardiac puncture into EDTA treated tubes and a portion of the liver was removed and rapidly frozen Liver portions were stored at −80° C. in liquid nitrogen for further analysis.

Lipid Analysis. Plasma was obtained by centrifugation of the blood sample for 10 minutes at 2500 rpm. Plasma cholesterol was determined using a WAKO Diagnostic Cholesterol II Assay.

Hepatic Lipase Assay. A portion of the liver was homogenized in normal saline containing 20 units of heparin per mL. After a 30 minute incubation at ambient temperature, the homogenate was centrifuged for 3 minutes at 8000g, and the supernatant collected for assay. Hepatic lipase activity was determined essentially by the method of Henderson et al., using $H^3$ triolein in an acacia emulsion as a substrate. Free fatty acids were separated from non-hydrolyzed substrate by the addition of fumed silica according to Borensztajn et al. and quantitated by liquid scintillation. (See: Henderson, A. D., Richmond, W., and Elkeles, R. S., "Hepatic and Lipoprotein Lipases Selectively Assayed in Postheparin Plasma.", Clin. Chem., 39/2, p. 218–223 (1993). Borensztajn, J., Reddy, M. N., and Gladstone, A. R., "A Simple Method for the Separation of Triacylglycerols from Fatty Acids Released in Lipase Assays.", J. Lipdid Res., 29, p. 1549–1552 (1988).)

The results using the compound of Example 5 demonstrate the potential for the methods of the current invention and are set out in Table 2.

TABLE 2

| | | (% of untreated control) | | |
|---|---|---|---|---|
| Compound | Dose mg/kg | Hepatic Lipase | Plasma Cholest. | Plasma Triglyc. |
| Ex. 5 (Exp.1) | 10 | 84 | 98 | 84 |
| | 100 | 75 | 82 | 83 |
| | 1000 | 18 | 13 | 50 |
| Ex. 5 (Exp.2) | 1000 | 25 | 11 | 74 |
| | 5000 | 19 | 3 | 39 |

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical formulation comprising an effective amount of a compound of formula I(a), where R, $R^1$, and $R^2$ are independently at each occurrence hydrogen, hydroxy, —O($C_1$–$C_4$ alkyl), —OCO($C_1$–$C_4$ alkyl), —OCOAr, —OCO$_2$($C_1$–$C_4$ alkyl), —OCO$_2$Ar, or $C_3$–$C_6$ cycloalkoxy; or a pharmaceutically acceptable salt thereof, (hereafter referred to as compounds of formula I(c)) and a pharmaceutically acceptable carrier, diluent, or excipient.

The total active ingredients in such formulations comprises from 0.1% to 99.9% by weight of the formulation. A typical daily dose will contain a nontoxic dosage level of from about 1 mg to about 600 mg/day of a compound of formula I(b) or I(c). Preferred daily doses generally will be from about 5 mg to about 80 mg/day.

Pharmaceutical formulations of the present invention can be prepared by procedures known in the art using well known and readily available ingredients. For example, the compounds of formula I(c) can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

Compounds of formula I(c) also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I(b) and I(c), generally, will be administered in a convenient formulation as determined by the attending physician. The following formulation examples are only illustrative and are not intended to limit the scope of the present invention.

FORMULATIONS

In the formulations which follow, "active ingredient" means a compound of formula I(c), or a pharmaceutically acceptable salt or solvate thereof.

Hard gelatin capsules are prepared using the following:

| Formulation 1 Gelatin Capsules | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

| Formulation 2 Tablets | |
|---|---|
| Ingredient | Quantity (mg/tablet) |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5 mg–1000 mg of active ingredient are made up as follows:

| Formulation 3 Tablets | |
|---|---|
| Ingredient | Quantity (mg/tablet) |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C.–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1 mg–1000 mg of medicament per 5 ml dose are made as follows:

| Formulation 4 Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5 Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6 Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7 Intravenous Solution | |
|---|---|
| Ingredient | Quantity |
| Active ingredient | 50 mg |
| Isotonic saline | 1,000 mL |

The solution of the above ingredients is intravenously administered to a patient at a rate of about 1 mL per minute.

We claim:

1. A method of inhibiting hyperlipidemia comprising administering to a mammal in need thereof an effective amount of a compound of formula I(b):

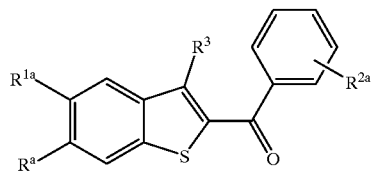

I(b)

wherein:

$R^a$, $R^{1a}$, and $R^{2a}$ are independently at each occurrence hydrogen, hydroxy, $C_1$–$C_4$ alkoxy, $C_3$–$C_6$ cycloalkoxy, —OCO($C_1$–$C_4$ alkyl), —OCOAr, —OCO$_2$($C_1$–$C_4$ alkyl), or CO$_2$Ar;

Ar is phenyl or substituted phenyl;

$R^3$ is hydrogen, $C_1$–$C_6$ alkyl, $C_3$–$C_6$ cycloalkyl, or a moiety of the formula (a), (b), or (c):

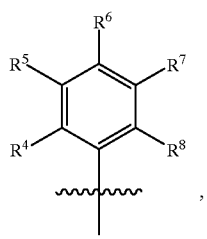

(a)

,

-continued

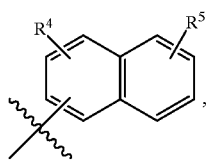
(b)

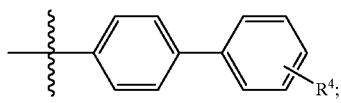
(c)

wherein $R^4$, $R^5$, $R^6$, $R^7$, and $R^8$ are independently at each occurrence hydrogen, fluoro, chloro, bromo, $C_1$–$C_4$ alkyl, $C_3$–$C_6$ cycloalkyl, or $C_1$–$C_4$ alkoxy; or a pharmaceutically acceptable salt or solvate thereof.

2. A method according to claim 1 wherein said mammal is a human.

3. A method according to claim 2 wherein said human is female.

4. A method according to claim 3 wherein said female is post-menopausal.

5. A method according to either claim 2 or claim 3 wherein the hyperlipidemia is hypercholesterolemia.

6. A method according to either claim 2 or claim 3 wherein the hyperlipidemia results in atherosclerosis.

7. A method according to claim 2 wherein said compound of formula I(b) is a compound wherein $R^{2a}$ is not hydrogen and $R^{1a}$ is hydrogen.

8. A method according to claim 7 wherein said compound of formula I(b) is a compound wherein $R^3$ is a moiety of formula (a) and $R^4$, $R^5$, $R^6$, $R^7$, and $R^8$ are all hydrogen.

9. A method according to claim 8 wherein $R^a$ and $R^{2a}$ are both methoxy.

10. A method according to claim 8 wherein $R^a$ and $R^{2a}$ are both hydroxy.

11. A method of inhibiting hyperlipidemia comprising administering to a mammal in need thereof an effective amount of a compound of the formula.

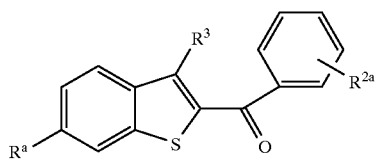

wherein:

$R^a$ is hydrogen, hydroxy, $C_1$–$C_4$ alkoxy, $C_3$–$C_6$ cycloalkoxy, —OCO($C_1$–$C_4$ alkyl), —OCOAr, —OCO$_2$($C_1$–$C_4$ alkyl), or —CO$_2$Ar;

Ar is phenyl or substituted phenyl;

$R^{2a}$ is hydroxy, $C_1$–$C_4$ alkoxy, $C_3$–$C_6$ cycloalkoxy, —OCO($C_1$–$C_4$ alkyl), —OCOAr, —OCO$_2$($C_1$–$C_4$ alkyl), or —CO$_2$Ar;

$R^3$ is hydrogen, $C_1$–$C_6$ alkyl, $C_3$–$C_6$ cycloalkyl, or a moiety of the formula (a), (b) or (c):

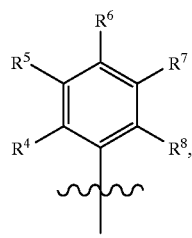
(a)

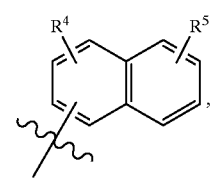
(b)

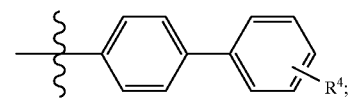
(c)

wherein $R^4$, $R^5$, $R^6$, $R^7$ and $R^8$ are each independently hydrogen, fluoro, chloro, bromo, $C_1$–$C_4$ alkyl, $C_3$–$C_6$ cycloalkyl or $C_1$–$C_4$ alkoxy, or a pharmaceutically acceptable salt or solvate thereof.

12. A method according to claim 11 wherein $R^3$ is a moiety of formula (a) and $R^4$, $R^5$, $R^6$, $R^7$ and $R^8$ are all hydrogen.

13. A method according to claim 12 wherein $R^{2a}$ is a hydroxy.

14. A method according to claim 12 wherein $R^{2a}$ is a $C_1$–$C_4$ alkoxy.

15. A method according to claim 12 wherein $R^a$ is a hydroxy.

16. A method according to claim wherein $R^a$ is a $C_1$–$C_4$ alkoxy.

17. A method according to claim 1 wherein $R_3$ is a phenyl group.

18. A method of inhibiting hyperlipidemia comprising administering to a mammal in need thereof an effective amount of a compound of the formula

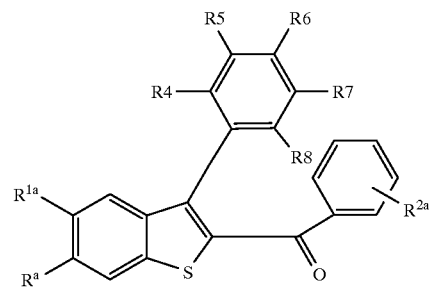

wherein:

$R^a$, $R^{1a}$, and $R^{2a}$ are each independently hydrogen, hydroxy, $C_1$–$C_4$ alkoxy, $C_3$–$C_6$ cycloalkoxy, —OCO ($C_1$–$C_4$ alkyl), —OCOAr, —OCO$_2$ ($C_1$–$C_4$ alkyl), or —CO$_2$Ar;

Ar is phenyl or substituted phenyl; and $R^4, R^5, R^6, R^7, R^8$, are each independently hydrogen, fluoro, chloro, bromo, $C_1$–$C_4$ alkyl, $C_3$–$C_6$ cycloalkyl or $C_1$–$C_4$ alkoxy, or a pharmaceutically acceptable salt or solvate thereof.

19. A method according to claim 18 wherein $R^a$ and $R^{1a}$ are hydrogen or hydroxy and wherein $R^a$ and $R^{1a}$ are not the same.

20. A method according to claim 18 wherein $R^{1a}$ is a hydrogen.

21. A method according to claim 20 wherein said compound of formula I(b) is 2-(4-cyclopentyloxybenzoyl)-3-phenyl-6-hydroxybenzo[b]thiophene.

22. A method according to claim 20 wherein said compound of formula I(b) is 2-(4-hydroxybenzoyl)-3-phenyl-benzo[b]thiophene.

23. A method according to claim 20 wherein said compound of formula I(b) is 2-(2-methoxybenzoyl)-3-phenyl-6-methoxybenzo[b]thiophene.

24. A method of inhibiting hyperlipidemia comprising administering to a mammal in need thereof an effective amount of 2-(4-hydroxybenzoyl-3-phenyl-6-hydroxybenzo[b]thiophene or a pharmaceutically acceptable salt or solvent thereof.

* * * * *